United States Patent [19]

Edwards et al.

[11] Patent Number: 5,591,125
[45] Date of Patent: *Jan. 7, 1997

[54] MEDICAL PROBE WITH STYLETS

[75] Inventors: Stuart D. Edwards, Los Altos; Hugh R. Sharkey, Redwood City; Ingemar H. Lundquist, Pebble Beach; Ronald G. Lax, Grass Valley; James A. Baker, Jr., Palo Alto, all of Calif.

[73] Assignee: Vidamed, Inc., Menlo Park, Calif.

[ * ] Notice: The term of this patent shall not extend beyond the expiration date of Pat. No. 5,421,819.

[21] Appl. No.: 470,621

[22] Filed: Jun. 6, 1995

Related U.S. Application Data

[63] Continuation of Ser. No. 61,647, May 13, 1993, Pat. No. 5,421,819, which is a continuation-in-part of Ser. No. 929,638, Aug. 12, 1992, Pat. No. 5,366,490, and Ser. No. 12,370, Feb. 2, 1993, Pat. No. 5,370,675.

[51] Int. Cl.⁶ ............................................. A61B 17/39
[52] U.S. Cl. .................................................... 604/22
[58] Field of Search ............................... 604/19–22, 53, 604/164, 280; 606/39, 45; 607/96, 98–102, 113, 115, 116, 138, 156; 601/2

[56] References Cited

U.S. PATENT DOCUMENTS

| 4,950,267 | 8/1990 | Ishihara et al. ............... 606/12 |
| 5,003,991 | 4/1991 | Takayama et al. ............ 128/784 |
| 5,421,819 | 6/1995 | Edwards et al. ............... 604/22 |

FOREIGN PATENT DOCUMENTS

| 2941060 | 4/1980 | Germany ........................ 606/6 |
| 3247793 | 7/1983 | Germany ........................ 606/6 |
| 2121675 | 9/1990 | Japan ........................... 604/22 |
| 9116859 | 11/1991 | WIPO .......................... 604/22 |
| 9210142 | 6/1992 | WIPO .......................... 604/22 |
| 9315664 | 8/1993 | WIPO .......................... 604/22 |

OTHER PUBLICATIONS

U.S. Patent application 07/832,115 Filed on Feb. 2, 1992.

*Primary Examiner*—Manuel Mendez
*Attorney, Agent, or Firm*—Flehr, Hohbach, Test, Albritton & Herbert

[57] ABSTRACT

A medical probe device of this invention comprising a catheter having a control end and a probe end. The probe end includes a stylet guide housing having at least one stylet port and stylet guide means for directing a flexible stylet outward through at least one stylet port and through intervening tissue to targeted tissues. A stylet is positioned in at least one of said stylet guide means, the stylet comprising a non-conductive sleeve having a RF electrode lumen and an optional a fluid supply lumen and a temperature sensor lumen therein. At least one portion of an opposed surface of the electrode lumen and the electrode can be spaced apart to define a liquid supply passageway for delivery of medicament liquid. The RF electrode enclosed within the non-conductive sleeve has a distal length optionally having at least one current focusing groove means thereon and a distal tip shaped to focus current crowding on its terminal end, whereby Rf current passing therefrom into surrounding tissue forms a lesion extending outward from the groove and tip. The focusing groove means can be a plurality of annular focusing grooves or a spiral focusing groove thereon.

11 Claims, 8 Drawing Sheets

MEDICAL PROBE WITH STYLETS

RELATIONSHIP TO COPENDING APPLICATION

This is a continuation of application Ser. No. 08/061,647, filed May 13, 1993, now U.S. Pat. No. 5,421,819 which is a continuation in part of application Ser. No. 07/929,638, filed Aug. 12, 1992, now U.S. Pat. No. 5,366,490 and a continuation in part of application Ser. No. 08/012,370, filed Feb. 2, 1993, now U.S. Pat. No. 5,370,675. A related copending application is application Ser. No. 08/063,364 entitled MEDICAL PROBE DEVICE WITH OPTIC VIEWING CAPABILITY filed concurrently herewith. The entire contents of all of the above application are hereby incorporated by reference.

FIELD OF THE INVENTION

This invention is directed to a unique device and method for penetrating body tissues for medical purposes such as tissue ablation and fluid substance delivery, for example. The device penetrates tissue to the precise target selected in order to deliver energy to the tissue and/or deliver substances. It limits this treatment to the precise preselected site, thereby minimizing trauma to normal surrounding tissue and achieving a greater medical benefit. This device is a catheter-like device for positioning a treatment assembly in the area or organ selected for medical treatment with one or more stylets in the catheter, mounted for extension from a stylet port in the side of the catheter through surrounding tissue to the tissue targeted for medical intervention.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of targeted tissues in the body or the proximity of the target tissue to easily damaged, critical body organs, nerves, or other components.

Benign prostatic hypertrophy or hyperplasia (BPH), for example, is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and dribbling. The association of BPH with aging has been shown to exceed 50% in men over 50 years of age and increases in incidence to over 75% in men over 80 years of age. Symptoms of urinary obstruction occur most frequently between the ages of 65 and 70 when approximately 65% of men in this age group have prostatic enlargement.

Currently there is no proven effective nonsurgical method of treatment of BPH. In addition, the surgical procedures available are not totally satisfactory. Currently patients suffering from the obstructive symptoms of this disease are provided with few options: continue to cope with the symptoms (i.e., conservative management), submit to drug therapy at early stages, or submit to surgical intervention. More than 430,000 patients per year undergo surgery for removal of prostatic tissue in the United States. These represent less than five percent of men exhibiting clinical significant symptoms.

Those suffering from BPH are often elderly men, many with additional health problems which increase the risk of surgical procedures. Surgical procedures for the removal of prostatic tissue are associated with a number of hazards including anesthesia related morbidity, hemorrhage, coagulopathies, pulmonary emboli and electrolyte imbalances. These procedures performed currently can also lead to cardiac complications, bladder perforation, incontinence, infection, urethral or bladder neck stricture, retention of prostatic chips, retrograde ejaculation, and infertility. Due to the extensive invasive nature of the current treatment options for obstructive uropathy, the majority of patients delay definitive treatment of their condition. This circumstance can lead to serious damage to structures secondary to the obstructive lesion in the prostate (bladder hypertrophy, hydronephrosis, dilation of the kidney pelves, chronic infection, dilation of ureters, etc.) which is not without significant consequences. In addition, a significant number of patients with symptoms sufficiently severe to warrant surgical intervention are therefore poor operative risks and are poor candidates for prostatectomy. In addition, younger men suffering from BPH who do not desire to risk complications such as infertility are often forced to avoid surgical intervention. Thus the need, importance and value of improved surgical and non-surgical methods for treating BPH is unquestionable.

High-frequency currents are used in electrocautery procedures for cutting human tissue especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using an electromagnetic energy which is rapidly dissipated and reduced to a non-destructive level by conduction and convection forces of circulating fluids and other natural body processes.

Microwave, radiofrequency, acoustical (ultrasound) and light energy (laser) devices, and tissue destructive substances have been used to destroy malignant, benign and other types of cells and tissues from a wide variety of anatomic sites and organs, Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave antenna through a duct to the zone of treatment and apply energy diffusely through the duct wall into the surrounding tissue in all directions. Severe trauma is often sustained by the duct wall during this cellular destruction process, and some devices combine cooling systems with microwave antennas to reduce trauma to the ductal wall. For treating the prostate with these devices, for example, heat energy is delivered through the walls of the urethra into the surrounding prostate cells in an effort to ablate the tissue causing the constriction of the urethra. Light energy, typically from a laser, is delivered to prostate tissue target sites by "burning through" the wall of the urethra. Healthy cells of the duct wall and healthy tissue between the nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

Application of liquids to specific tissues for medical purposes is limited by the ability to obtain delivery without traumatizing intervening tissue and to effect a delivery limited to the specific target tissue. Localized chemotherapy, drug infusions, collagen injections, or injections of agents which are then activated by light, heat or chemicals would be greatly facilitated by a device which could conveniently and precisely place a fluid (liquid or gas) supply catheter opening at the specific target tissue.

OBJECTS AND SUMMARY OF THE INVENTION

It is an object of this invention to provide a device and method for penetrating tissue, through intervening tissues to the precise target tissue selected for a medical action such as tissue ablation and/or substance delivery, limiting this activity to the precise preselected site, thereby minimizing the trauma and achieving a greater medical benefit.

It is another object of this invention is to provide a device and method for tissue ablation of body tissues which delivers the therapeutic energy directly into targeted tissues while minimizing effects on its surrounding tissue.

It is a still further object of this invention is to provide a device and method for introducing fluid treatment agents such as flowable liquids and gases, with greater precision and ease to a specific location in the body.

Another object of this invention is to provide a thermal destruction device which gives the operator more information about the temperature and other conditions created in both the tissue targeted for treatment and the surrounding tissue. In addition, it will provide more control over the physical placement of the stylet and over the parameters of the tissue ablation process.

In summary, the medical probe device of this invention comprises a catheter having a control end and a probe end. The probe end includes a stylet guide housing having at least one stylet port and stylet guide means for directing a flexible stylet outward through at least one stylet port and through intervening tissue to targeted tissues. A stylet is positioned in at least one of said stylet guide means, the stylet comprising a non-conductive sleeve having at least two and preferably three lumina therein. An RF electrode lumen terminates at a distal port in the distal end of the non-conductive sleeve, and a radiofrequency electrode is positioned in the RF electrode lumen for longitudinal movement therein through the distal port. Preferably, at least one portion of an opposed surface of the electrode lumen and the electrode are spaced apart to define a liquid supply passageway for delivery of medicament liquid. A second optional fluid passage lumen terminates at a distal port in the distal end of the non-conductive sleeve and comprises means passing fluid therethrough.

A temperature sensor third lumen terminates in a sealed closure adjacent the distal end of the non-conductive sleeve. At least one and preferably a plurality of temperature sensing devices such as thermocouples are positioned in the third lumen, the leads extending through the lumen. One preferred embodiment has two temperature sensing devices positioned in the third lumen, one temperature sensing device being positioned within about 1 mm of the distal end of the non-conductive sleeve, and the second temperature sensing device being positioned at least 3 mm and preferably from 3 to 6 mm from the distal end of the non-conductive sleeve.

In summary, another embodiment of this invention comprises a catheter having a control end and a probe end, the probe end including a stylet guide housing having at a stylet port and stylet guide means for directing a flexible stylet outward through the stylet port and through intervening tissue to targeted tissues. A stylet is positioned in at least one of said stylet guide means, the stylet comprising an electrical conductor enclosed within a non-conductive sleeve. The electrode has a distal length having at least one current focusing groove means thereon and a distal tip shaped to focus current on its terminal end, whereby RF current passing therefrom into surrounding tissue forms a lesion extending outward from the groove and tip. In one preferred embodiment, the distal length has a plurality of annular focusing grooves or a spiral focusing groove thereon.

Preferably at least a part of the electrode is enclosed within a support tube having sufficient strength to maintain electrode linearity when the electrode is directed outward through the stylet port.

DETAILED DESCRIPTION OF THE INVENTION

The device of this invention provides a precise controlled positioning of a treatment stylet in a tissue targeted for treatment, destruction or sampling from a catheter positioned in the vicinity of the target tissue.

The term "stylet" as used hereinafter is defined to include both solid and hollow probes which are adapted to be passed from a catheter port through normal tissue to targeted tissues. The stylet is shaped to facilitate easy passage through tissue. It can be a solid wire, thin rod, or other solid shape or it can be a thin hollow tube or other shape having a longitudinal lumen for introducing fluids to or removing materials from a site. The stylet can also be a thin hollow tube or other hollow shape, the hollow lumen thereof containing a reinforcing or functional rod or tube such as a laser fiber optic. The stylet preferably has a sharpened end to reduce resistance and trauma when it is pushed through tissue to a target site.

The stylet can be designed to provide a variety of medically desired treatments of a selected tissue. As a radiofrequency electrode or microwave antenna, it can be used to ablate or destroy targeted tissues. As a hollow tube, it can be used to deliver a treatment fluid such as a liquid to targeted tissues. The liquid can be a simple solution or a suspension of solids, for example, colloidal particles, in a liquid. Since the stylet is very thin, it can be directed from the catheter through intervening normal tissue with a minimum of trauma to the normal tissue.

The device and method of this invention provide a more precise, controlled medical treatment which is suitable for destroying cells of medically targeted tissues throughout the body, both within and external to body organs. The device and method are particularly useful for treating benign prostate hyperplasia (BPH), and the device and its use are hereinafter described with respect to BPH, for purposes of simplifying the description thereof. It will be readily apparent to a person skilled in the art that the device and method can be used to destroy body tissues in any body cavities or tissue locations that are accessible by percutaneous or endoscopic catheters, and is not limited to the prostate. Application of the device and method in all of these organs and tissues are intended to be included within the scope of this invention.

BPH is a condition which arises from the replication and growth of cells in the prostate and the decrease of cell death rate, forming glandular and stromal nodules which expand the prostate and constrict the opening of the prostatic urethra. Glandular nodules are primarily concentrated within the transition zone, and stromal nodules within the periurethral region. Traditional treatments of this condition have included surgical removal of the entire prostate gland, digital removal of the adenoma, as well as transurethral resection of the urethral canal and prostate to remove tissue and widen the passageway. One significant and serious complication associated with these procedures is iatrogenic sterility. More recently, laser treatment has been employed to remove tissue, limiting bleeding and loss of body fluids. Balloons have also been expanded within the urethra to enlarge its diameter, with and without heat, but have been found to have significant limitations.

Microwave therapy has been utilized with some success by positioning a microwave antenna within the prostatic urethra and generating heat in the tissue surrounding the urethra with an electromagnetic field. Coolants are sometimes applied within the catheter shaft to reduce the temperature of the urethral wall. This necessitates complicated mechanisms to provide both cooling of the immediately adjacent tissues while generating heat in the more distant prostatic tissue. This technique is similar to microwave hyperthermia. Similarly, radiofrequency tissue ablation with electrodes positioned within the urethra exposes the urethral wall to destructive temperatures. To avoid this, low temperature settings required to protect the urethra must be so low that the treatment time required to produce any useful effect is unduly extended, e.g. up to three hours of energy application.

One embodiment of the device of this invention uses the urethra to access the prostate and positions RF electrode stylets directly into the tissues to be destroyed. The portion of the stylet conductor extending from the urethra to targeted tissues is enclosed within a longitudinally adjustable sleeve shield which prevents exposure of the tissue adjacent to the sleeve to the RF current. The sleeve movement is also used to control the amount of energy per unit surface area which is delivered by controlling the amount of electrode exposed. Thus the ablative destruction is confined to the tissues targeted for destruction, namely those causing the constriction. Other aspects of the invention will become apparent from the drawings and accompanying descriptions of the device and method of this invention. It will be readily apparent to a person skilled in the art that this procedure can be used in many areas of the body for percutaneous approaches and approaches through body orifices.

Figure 1:
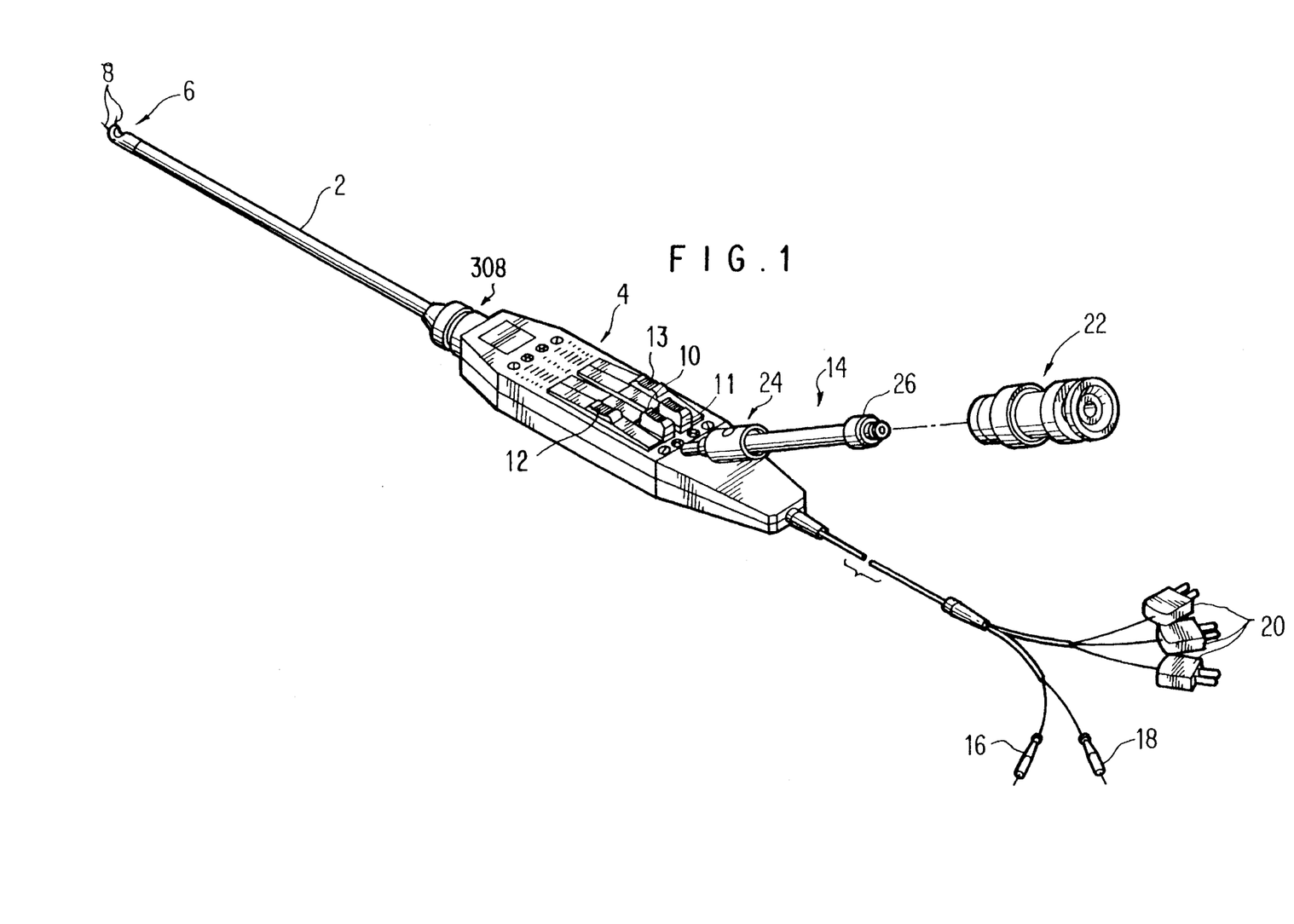
FIG. 1 is an isometric view of an RF ablation catheter embodiment of this invention with an fiber optic viewing accessory.

FIG. 1 is an isometric view of an RF ablation catheter embodiment of this invention with a fiber optic viewing accessory. The flexible catheter 2, attached to handle 4, has a terminal stylet guide 6 with two stylets 8. The handle has stylet electrode tabs 10 and 11 and sleeve tabs 12 and 13 as will be described in greater detail hereinafter. The handle 4 is also connected to a optical viewing assembly 14 and RF power connector 16, transponder connector 18 and thermocouple connectors 20. The portions of the catheter 2 leading from the handle 4 to the stylet guide tip 6 can optionally has a graduated stiffness. For example, the catheter can be designed to be more stiff near the handle and more flexible near the tip, or any other stiffness profiles. The catheter can be constructed of an inner slotted stainless steel tube with outer flexible sleeve such as is described in U.S. Pat. No. 5,322,064, the entire contents of which are incorporated herein by reference. It can also be made of coiled or braided wire to which an outer sleeve is bonded.

The fiber optic viewing assembly in this embodiment includes a lens focusing assembly 22, a lens viewing assembly support connector 24 assembly attached to a male quick disconnect connector 26 by flexible tubing 28.

Figures 2, 7:
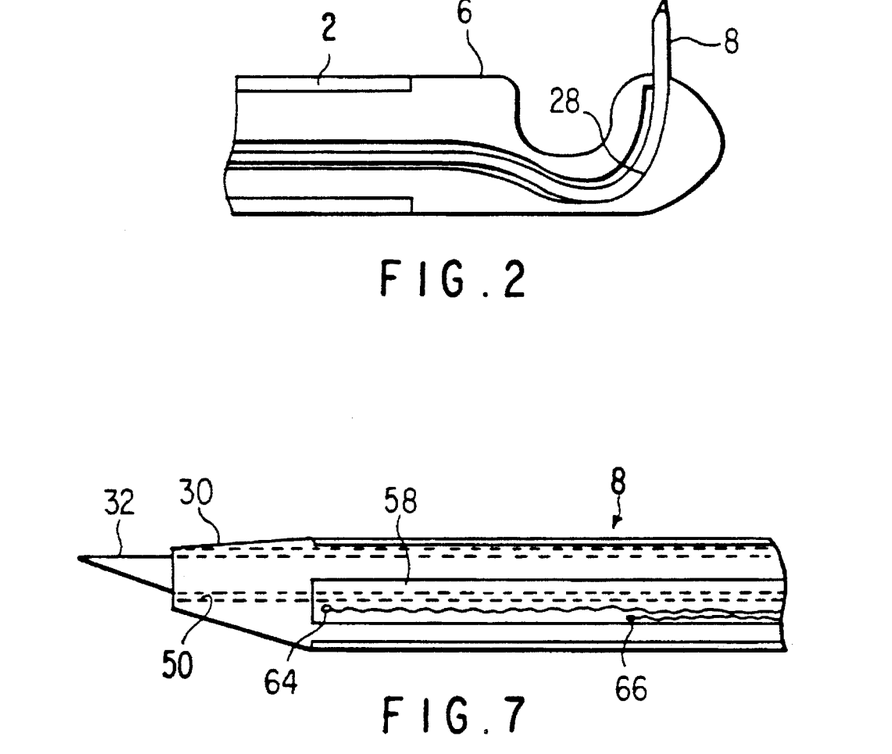
FIG. 2 is a cross-sectional view of a catheter of FIG. 1 showing details of the stylet guide housing.
FIG. 7 is a cross-sectional side view of the trilumen stylet tip shown in FIG. 3 taken along line 7—7 of FIG. 6.

FIG. 2 is a cross-sectional view of a catheter of FIG. 1 showing details of the stylet guide housing. The stylet guide housing 6 has a curved passageway 28 through which the stylet 8 is extended into the tissue to be treated. Further details of these components are described in copending applications Ser. No. 08/012,370, filed Feb. 2, 1993, and application Ser. No. 08/063,364, filed May 13, 1993.

Figure 3:
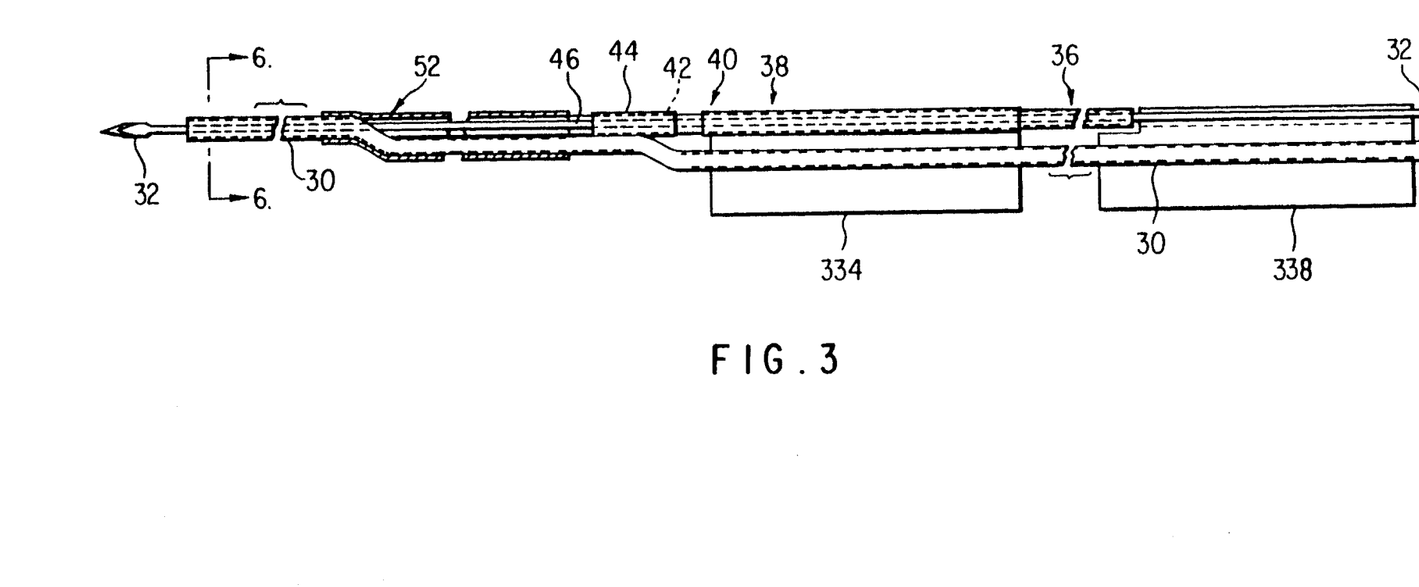
FIG. 3 is a side view of the stylet and lumen assembly of this invention.

FIG. 3 is a side view of the stylet and lumen assembly of this invention. The key components of the stylet of this embodiment are an insulating sleeve 30 and an electrode 32 extending therethrough. The electrode 32 has a sharpened tip, in this embodiment a broadened spear tip. The proximal end of the electrode and sleeve are connected by respective sleeve connector 334 and electrode connector 338 to handle sleeve and electrode slides described in greater detail hereinafter with respect to FIGS. 10 and 13. An electrode support tube 36 extends from the electrode connector 338 to the area 38 of the sleeve connector 334 to transmit compressive pressure without collapsing the electrode 32. An insulating sleeve support tube 40 made of shrink tubing extends from the sleeve connector 334 to the beginning or proximal end 42 of the outer tubing 44. Tubing 44 joins the support tubing to the control tube 46. The control tube 46 supporting both the electrode and insulating sleeve extends to the junction 48 (see FIG. 4) of the electrode lumen passageway 50 and the electrode 32. In this manner, support is provided over the length of the stylet extending from the handle to the trilumen tip, preventing collapse or loss of linearity of the highly flexible electrode when it is pushed through the stylet guide housing.

Figure 4:
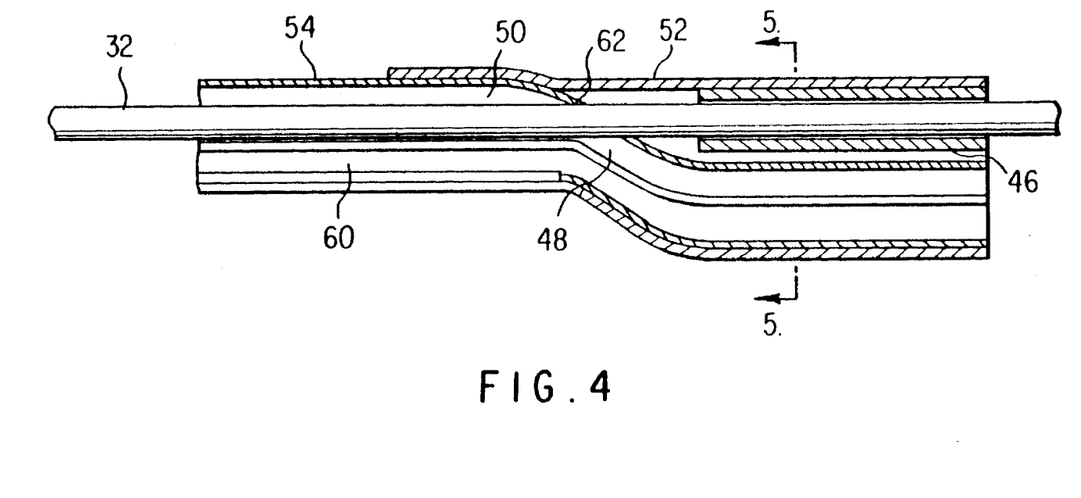
FIG. 4 is a cross-sectional side view of the of the junction of the stylet and control tube assembly taken along the central axis of the tubing.
Figure 5:
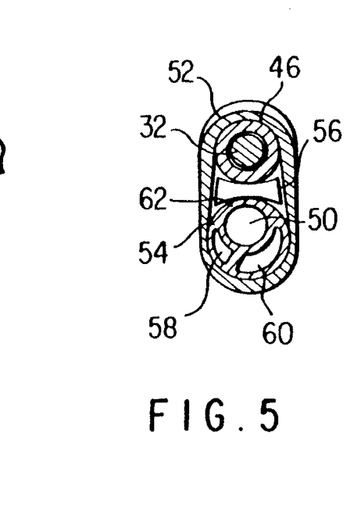
FIG. 5 is a cross-sectional view of the junction of the stylet and control tube assembly taken along the line 5—5 of FIG. 4.

FIG. 4 is a side elevational view of the in section junction of the stylet and control tube assembly along the central axis of the tubing, and FIG. 5 is a cross-sectional view of the junction of the stylet and control tube assembly taken along the line B—B of FIG. 4. At the junction 48, the electrode 32 extends through the upper electrode lumen wall 62 and enters the electrode lumen 50. The outer tubing 52 encloses and supports both the distal ends of the control tubing 46 a trilumen sleeve tube 54.

Referring to FIG. 5, the space 56 between the control tube 46 and the trilumen sleeve tube 54 can be filled with an adhesive to secure them together. The trilumen sleeve tube 54 includes electrode lumen 50, a temperature sensor lumen 58 and a fluid supply lumen 60 for supply of optional fluids such as antibiotics or anesthetics to the area of treatment.

Figure 6:
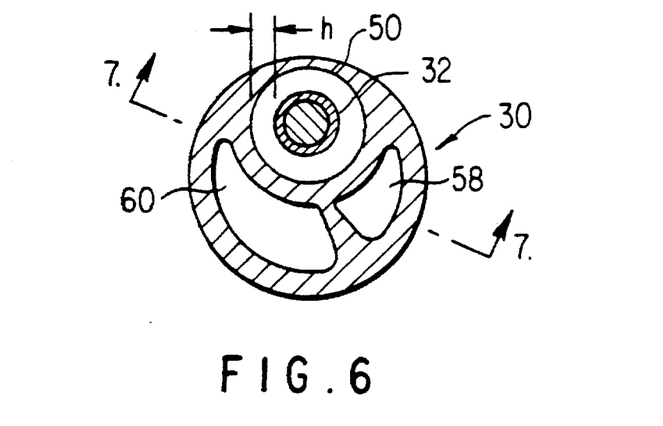
FIG. 6 is a cross-sectional view of a trilumen stylet of this invention taken along the line 6—6 in FIG. 3.

FIG. 6 is a cross-sectional view of a trilumen stylet of this invention taken along the line 6—6 in FIG. 3. The trilumen sleeve 30 is an insulating sleeve for the electrode 32 and includes the additional temperature sensor lumen 58 and liquid supply lumen 60. The inner surface of the electrode lumen 50 can be spaced from the outer surface of the electrode by a distance "h" which can be, for example, from about 1 to 3 mm to define an additional liquid supply conduit with an approximate annular cross-section.

FIG. 7 is a cross-sectional side view of the trilumen stylet tip shown in FIG. 6 taken along the line 7—7. The terminal end of the temperature sensor lumen 58 is sealed to protect the electrical components. Thermocouple 64 is placed at the distal end of the sleeve 30 to monitor the temperature of the tissue surrounding the electrode 32 and is preferably less than about 1 mm from the exposed electrode. Thermocouple 66 is placed at least about 3 mm and preferably from about 3 to 6 mm from the tip of sleeve 30 to monitor the temperature of the duct wall (such as the urethra) through which the stylet is extended. This is provided to ensure the duct wall temperature does not reach destructive levels when the RF treatment of tissue surrounding the extended electrode is underway.

Figure 8:
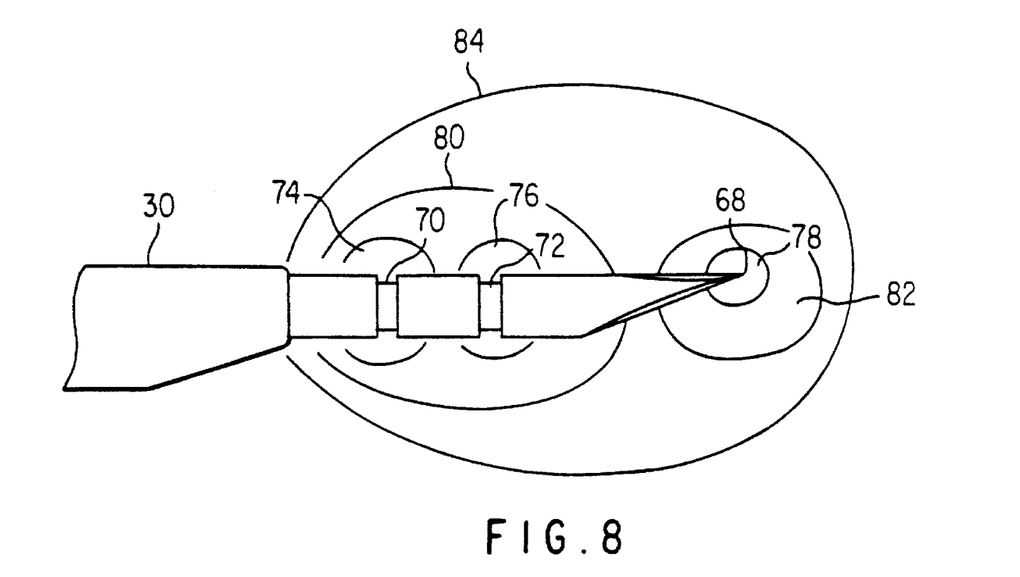
FIG. 8 is a plane view of the annular groove embodiment of the current density focusing electrode of this invention.

FIG. 8 is a plane view of the annular groove embodiment of the current density focusing electrode of this invention. In this embodiment, the electrode is ground to a single current focusing sharp tip 68 without secondary corner or other sharp edges which could also focus or crowd current. Additional current focusing can be provided along the electrode surface by the annular grooves 70 and 72. The temperature of the tissue surrounding the electrode initially increases in initial zones 74, 76 and 78. The elevated temperature zone then extends to two intermediate zones 80 and 82, as the zones from the grooves merge. Thereafter all of the elevated temperature zones merge to form the single oval zone lesion 84. Use of these current focusing grooves 70 and 72 produces a more symmetrical lesion.

Figure 9:
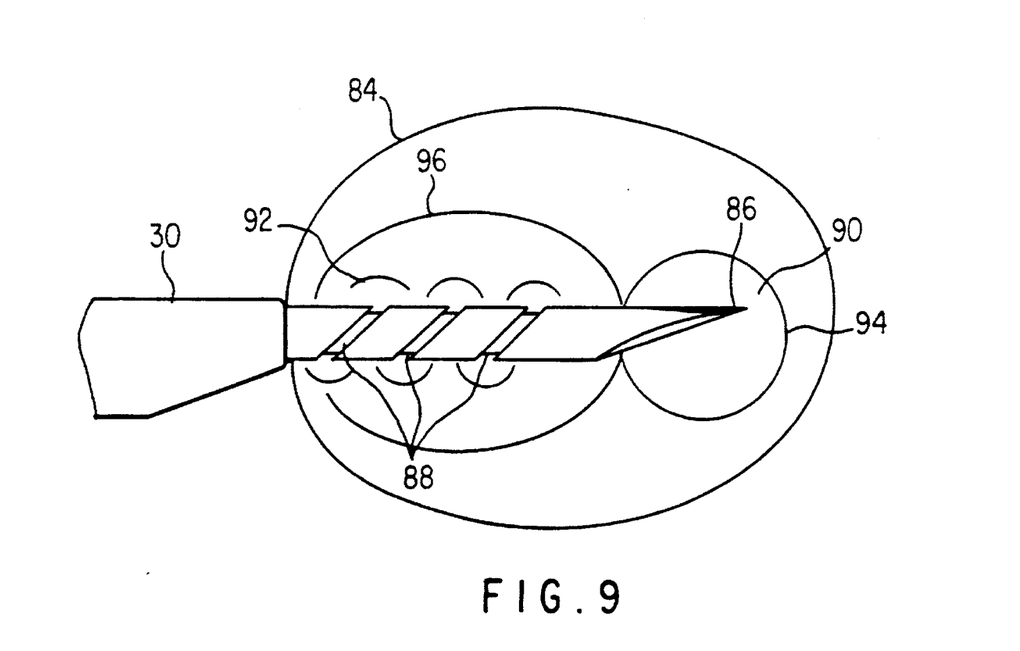
FIG. 9 is a plane view of the spiral groove embodiment of the current density focusing electrode of this invention. position and the sleeve partially retracted therefrom.

FIG. 9 is a plane view of the spiral groove embodiment of the current density focusing electrode of this invention. In this embodiment, the electrode is also ground to a single current focusing sharp tip 86 without secondary sharp corners or edges which could also focus or crowd current. Additional current focusing can be provided along the electrode surface by at least one spiral or helical groove 88. The temperature of the tissue surrounding the electrode initially increases in the initial tip zone 90 and spiral zone 92. The elevated temperature zone then extends to two intermediate zones 94 and 96, as the spiral zone 92 merges to form a single zone 96. Thereafter all of the elevated temperature zones merge to form the single oval zone lesion 98. Use of the spiral focusing groove 88 provides a more symmetrical lesion.

Figure 10:
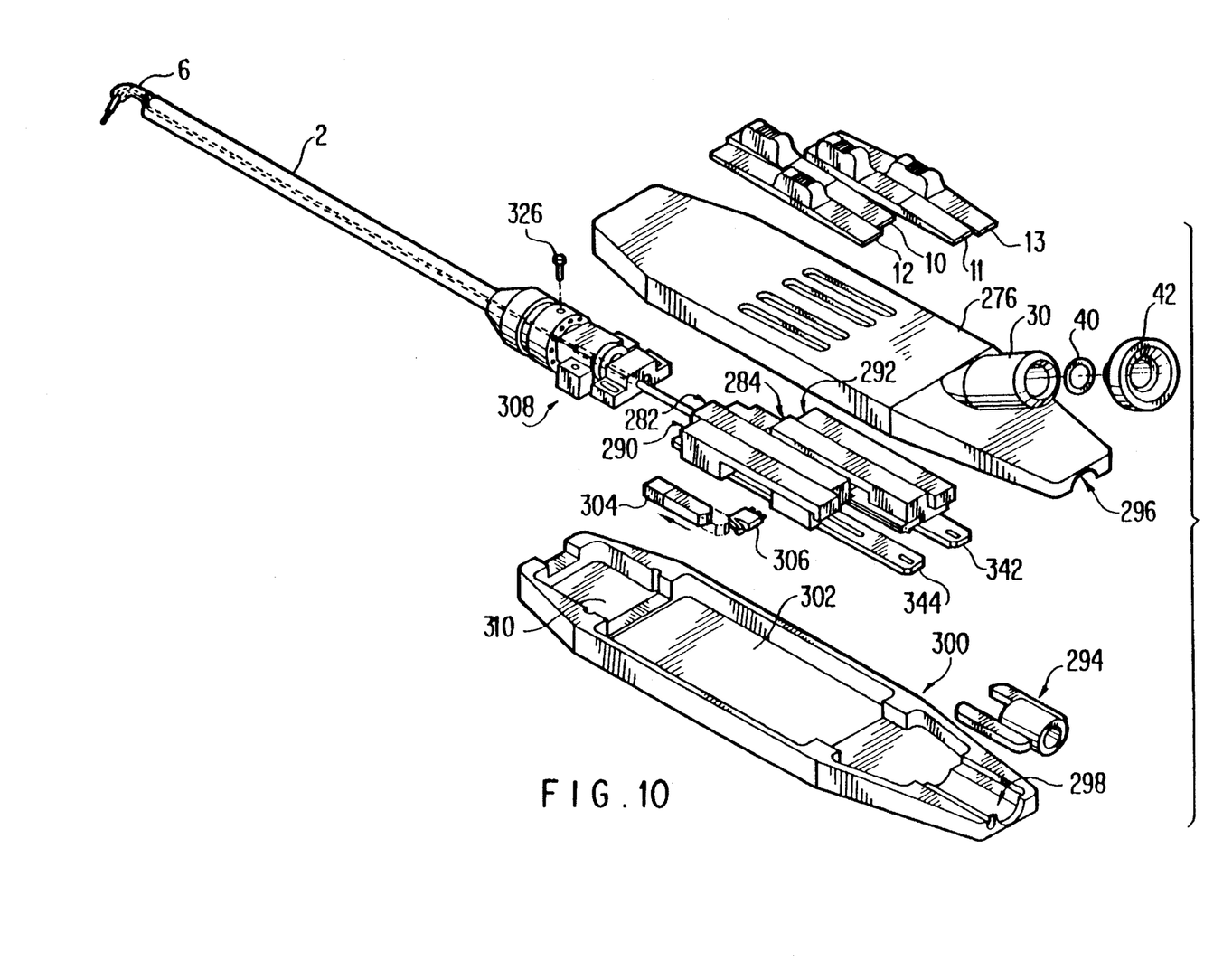
FIG. 10 is an exploded view of the RF ablation catheter shown in FIG. 1.

FIG. 10 is an exploded view of the RF ablation catheter assembly shown in FIG. 1. The upper handle plate 276 has two central slots 278 and 280 through which the electrode control slides 11 are attached to respective left electrode slide block 282 and right electrode slide block 284. Sleeve control slides 13 are attached through outer slots 286 and 288 to respective left sleeve slide block 290 and right sleeve slide block 292. Fiber optic receptor housing 30 is mounted on the proximal surface of the upper handle plate 276. The electrical receptor 294 is received in respective cavities 296 and 298 in the upper handle plate 276 and lower handle plate 300 attached thereto. The lower handle plate 300 has a central cavity 302 which accommodates the electrode and sleeve slide blocks and associated elements.

Microswitch activator blocks 304 (only left sleeve block shown) are connected to the sleeve slide blocks 290 and 292. They are positioned to actuate the microswitches 306 when the respective sleeve block (and sleeve attached thereto) have been advanced. The microswitches 306 hold the respective RF power circuits open until the respective sleeves are advanced to a position beyond the urethra wall and into the prostate to prevent direct exposure of the urethra to the energized RF electrodes. Extension of the sleeve 5 mm beyond the guide is usually sufficient to protect the urethra.

The tension-torque tube assembly 308 (see FIG. 11) is mounted in the distal end of the housing in the receptor 310.

Figures 11, 12:
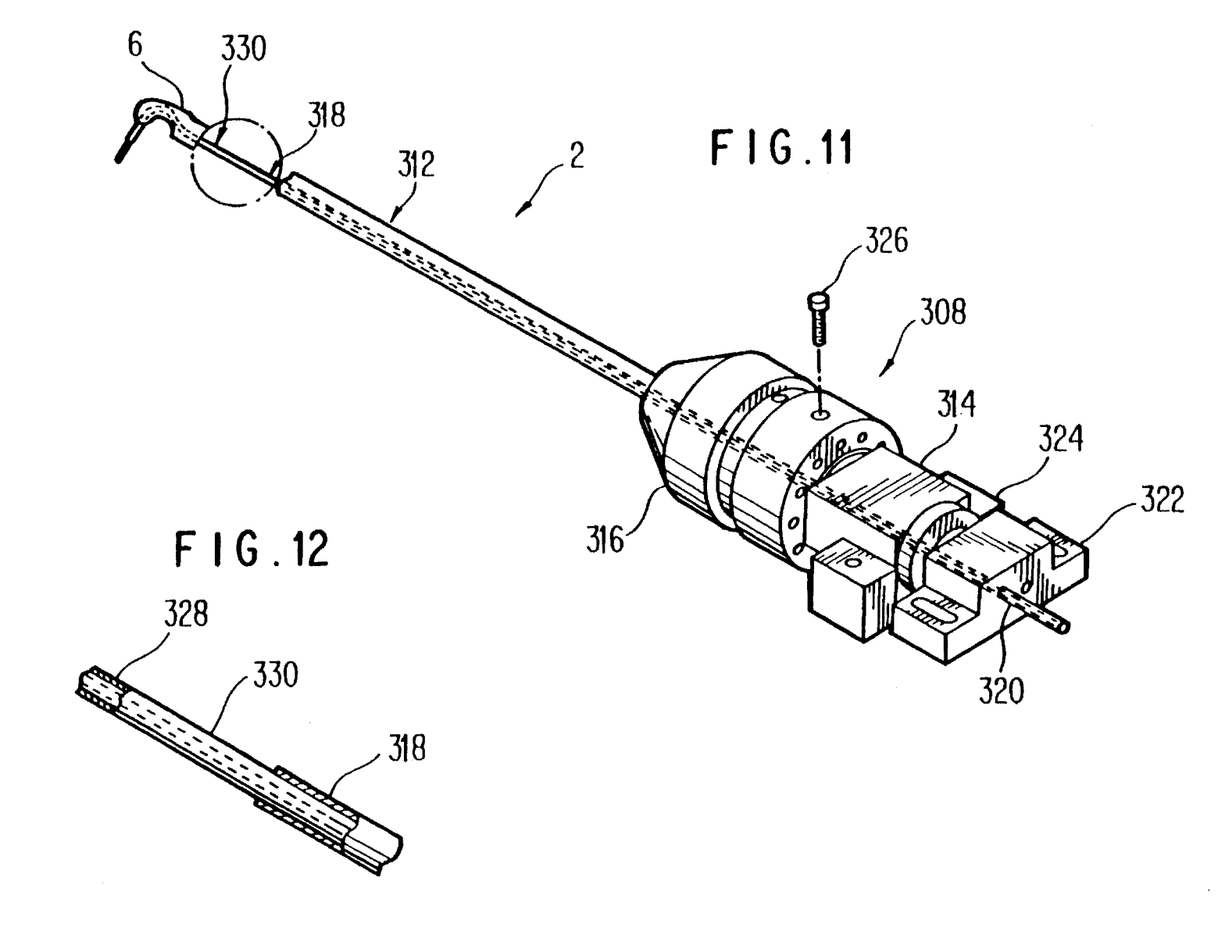
FIG. 11 is an isometric view of the adjuster block and tension tube assembly of the RF ablation catheter shown in FIG. 10.
FIG. 12 is a detailed view "A" of the tension tube connections shown in FIG. 11.

FIG. 11 is an isometric view of the adjuster block and tension tube assembly 308 of the RF ablation catheter shown in FIG. 10. The torque tube 312 extends from the torque coupler 314 through the twist control knob 316 to the stylet guide 6. Bending flexure of the torque tube 312 during use lengthens the path from the handle to the guide tip 6. To prevent a resulting retraction of the stylet sleeve and electrode components when the torque tube 312 is flexed, a tension tube 318 having a fixed length and diameter smaller than the inner diameter of the torque tube 312 is provided. The distal end of the tension tube 318 is securely attached to the stylet guide 6, and the proximal end 320 is secured to the adjuster block 322, for example by an adhesive. The axial position of the adjuster block 322 can be adjusted to ensure the stylets 8 are initially positioned just inside the outlet ports in the stylet guide 6. Torque coupler 314 is mounted on the coupler block 324. Twist control knob stop pin 326 extends into a grove (not shown) and limits rotation of the control knob 316.

FIG. 12 is a detailed view "A" of the distal end tension tube connections of the tension tube shown in FIG. 11. The tension tube 318 is securely connected to the proximal end 328 of the stylet guide 6, for example by a length of shrink tubing 330.

Figure 13:
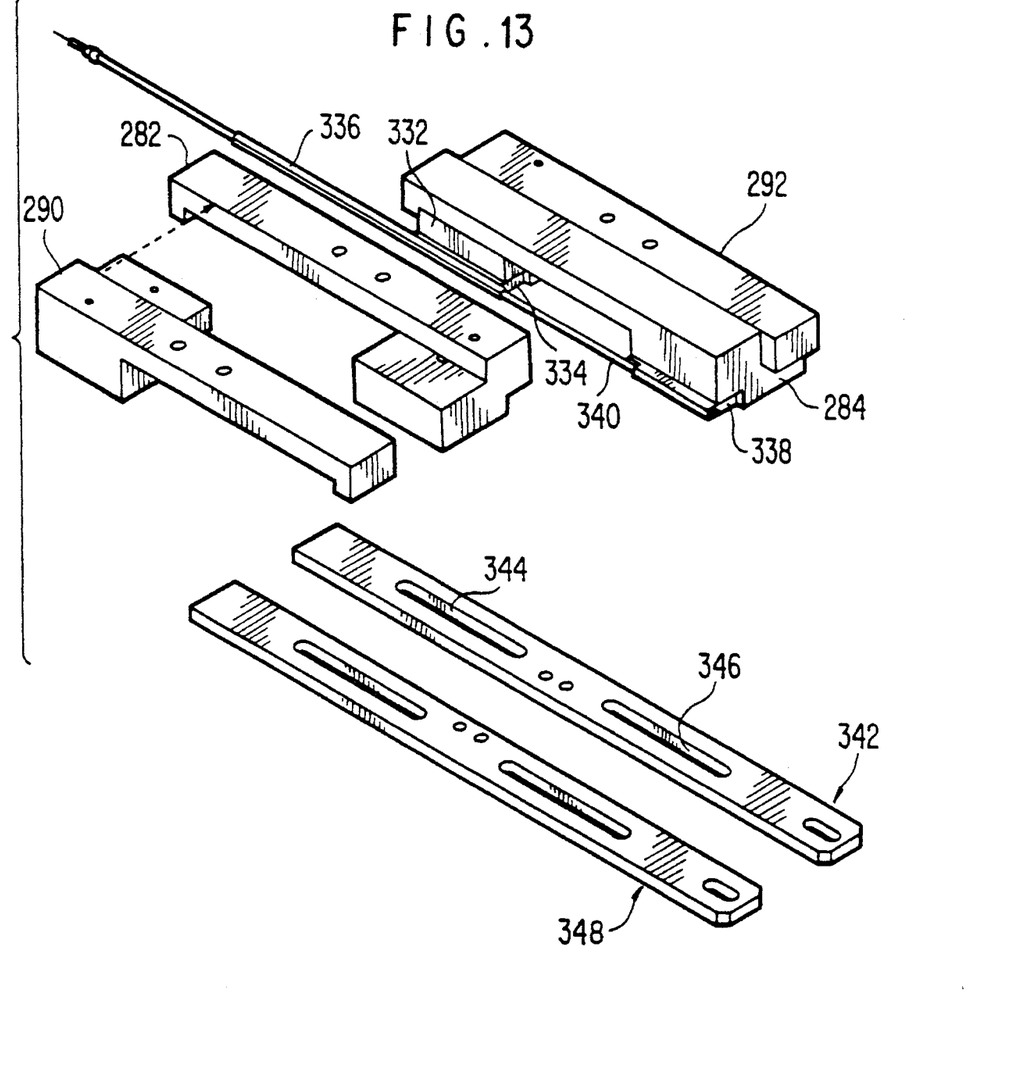
FIG. 13 is an exploded view of the sleeve and electrode slide block assembly of the embodiment shown in FIG. 10.

FIG. 13 is an exploded view of the sleeve and electrode slide block assembly of the embodiment shown in FIG. 10. The right sleeve slide block 292 has a projection 332 which extends inward under the right electrode slide block 284. Right sleeve connector 334 is mounted to the inner end of the projection 332, secured to the end of the proximal end of the sleeve 336. Right electrode connector 338 is attached to an inner surface of the electrode slide block 284 and is secured to the proximal end of electrode 340. The right sleeve and electrode slide blocks 292 and 284 are slidingly attached to the right friction adjustment rail 342 by screws (not shown) through slots 344 and 345, the screws being adjustable to provide sufficient friction between the blocks and the rail 342 to provide secure control over the stylet movement. The left sleeve slide block 290 and left electrode slide block 282 are mirror replicas of the right blocks and are similarly mounted on the left friction rail 348. The left sleeve and electrodes are not shown.

Although preferred embodiments of the subject invention have been described in some detail, it is understood that obvious variations can be made without departing from the spirit and the scope of the invention as defined by the appended claims.

We claim:

1. A medical probe device for use in a human body comprising a catheter having a control end portion and a probe end portion, the control end portion including handle means for permitting the probe end portion to be inserted into the body to perform a procedure therein, a longitudinally-extending flexible stylet slidably mounted in the probe end portion of the catheter, means carried by the handle means and connected to the flexible stylet for extending the flexible stylet outward from the probe end portion through intervening tissue to targeted tissue, the flexible styler including a radio frequency electrode and a non-conductive sleeve mounted about the radio frequency electrode and extending longitudinally thereof so as to expose a selected portion of the radio frequency electrode to the targeted tissue whereby upon the supply of radio frequency energy to the electrode the targeted tissue is ablated while the intervening tissue is protected by the non-conductive sleeve from radio frequency energy supplied to the electrode, the non-conductive sleeve being provided with a longitudinally-extending lumen for permitting a liquid to be delivered into the body.

2. A medical probe device of claim 1 wherein the radio frequency electrode has an outer surface and the non-conductive sleeve has an inner surface opposing said outer surface, the outer and inner surfaces being spaced apart to define a liquid supply passageway for delivery of liquid.

3. A medical probe device of claim 1 wherein the non-conductive sleeve is provided with an additional longitudinally-extending lumen and the radio frequency electrode is slidably disposed in the additional lumen to permit the selected portion of the radio frequency electrode to be adjusted.

4. A medical probe device of claim 1 wherein the non-conductive sleeve has a distal extremity, at least one temperature sensing means carded by the distal extremity of the non-conductive sleeve.

5. A medical probe device of claim 4 wherein the temperature sensing means is a thermocouple, electrical leads extending through the non-conductive sleeve to the temperature sensing means.

6. A medical probe device of claim 4 wherein the distal extremity of the non-conductive sleeve has a distal end, an additional temperature sensing means carried by the distal extremity, the first-named temperature sensing means being positioned within about 1 mm from the distal end of the non-conductive sleeve and the additional temperature sensing means being positioned at least about 3 mm from the distal end of the non-conductive sleeve.

7. A medical probe device of claim 6 wherein the temperature sensing means are thermocouples, electrical leads extending through the non-conductive sleeve to the temperature sensing means.

8. A medical probe device of claim 4 wherein the non-conductive sleeve is provided with an additional longitudinally-extending lumen, the temperature sensing means disposed within the additional lumen at the distal extremity of the non-conductive sleeve.

9. A medical probe device of claim 1 wherein the non-conductive sleeve has a distal end and the lumen extends through the distal end for permitting a liquid to be delivered to the targeted tissue.

10. A medical probe device for medical treatment of a prostate through a urethra defined by a urethral wall comprising a catheter having a control end portion and a probe end portion, the control end portion including handle means for permitting the probe end portion to be inserted into the urethra to perform a procedure in the prostate, the catheter having a length so that when the probe end portion is in the vicinity of the prostate the control end portion is outside of the urethra, a longitudinally-extending flexible styler slidably mounted in the probe end portion of the catheter, stylet guide means carried by the probe end portion for directing the flexible styler outward from the probe end portion through the urethral wall to targeted tissue in the prostate, the flexible styler including a radio frequency electrode and an insulating sleeve slidably mounted on the radio frequency electrode so as to expose a selected portion of the radio frequency electrode to the targeted tissue whereby upon the supply of radio frequency energy to the electrode the targeted tissue is ablated while the urethral wall is protected by the insulating sleeve from radio frequency energy supplied to the electrode, the insulating sleeve being provided with a longitudinally-extending lumen for permitting a liquid to be delivered to the targeted tissue.

11. A medical probe device of claim 10 wherein the insulating sleeve has a distal extremity, temperature sensing means carded by the distal extremity of the insulating sleeve.

* * * * *